United States Patent [19]
Forsythe et al.

[11] Patent Number: 5,935,660
[45] Date of Patent: Aug. 10, 1999

[54] TREATMENT OF POTATO STORAGE FACILITIES WITH AEROSOLS DERIVED FROM SOLID CIPC

[76] Inventors: Darol Forsythe, 15401 Cartwright Rd., Boise, Id. 83703; John M. Forsythe, 4277 Balivi La., Nampa, Id. 83687

[21] Appl. No.: 08/777,915

[22] Filed: Dec. 23, 1996

Related U.S. Application Data

[60] Provisional application No. 60/009,451, Dec. 29, 1995.

[51] Int. Cl.$^6$ ................................. B05D 1/02; B05D 1/08
[52] U.S. Cl. ......................... 427/446; 427/447; 427/421; 427/422; 426/307; 426/312; 426/419; 239/290; 239/296; 239/423; 239/424; 239/543
[58] Field of Search ..................................... 427/446, 447, 427/421, 422; 426/307, 312, 419; 239/290, 296, 423, 424, 543

[56] References Cited

U.S. PATENT DOCUMENTS

| | | | |
|---|---|---|---|
| 3,857,511 | 12/1974 | Govindan | 239/11 |
| 4,226,179 | 10/1980 | Sheldon, III et al. | 99/475 |
| 4,887,525 | 12/1989 | Morgan | 99/476 |
| 5,723,184 | 3/1998 | Yamamoto | 427/421 |

*Primary Examiner*—Timothy Meeks
*Attorney, Agent, or Firm*—Trask, Britt & Rossa

[57] ABSTRACT

Techniques for melting and forming aerosols from solid CIPC are disclosed. Solid CIPC in block form is convenient to ship and to handle. Solid CIPC in block form appears to have a consistency of solid paraffin wax. Solid CIPC is melted by controlled techniques to form a substantially pure liquid stream of CIPC. The molten or liquid stream of CIPC is converted to an aerosol of CIPC either by a pressurized, hot air stream or by a combustion gas stream.

12 Claims, 6 Drawing Sheets

TREATMENT OF POTATO STORAGE FACILITIES WITH AEROSOLS DERIVED FROM SOLID CIPC

BACKGROUND OF THE INVENTION

1. Priority Claim

Under the provisions of 35 U.S.C. §1.19(e), this application claims the priority of Provisional Patent Application Serial No. 60/009,451, filed Dec. 29, 1995.

2. Field

This invention relates generally to the treatment of vegetable storage facilities and, in particular, to potato storage facilities with aerosols of CIPC.

3. State of the Art

Potatoes are frequently stored from harvest time for a number of months until spring or, often times, the following summer. Typically, the potatoes are stored in storage facilities which are ventilated and humidified. Air circulation is maintained inasmuch as potatoes undergo respiration when stored which gives off $CO_2$, other chemicals and heat. It has long been known that unless specific steps or techniques are employed after storage that potatoes will sprout within a few months of initial storage and render the whole pile of potatoes interlocked and useless. Storage at temperatures of from about 42° to 45° F. is generally practical to minimize sprouting.

It is known in the art to apply sprout inhibitors of various types to potatoes to prevent sprouting during storage. One of the earlier patents relating to this is the Plant patent, U.S. Pat. No. 3,128,170, related to a method for applying isopropyl-N-chlorophenylcarbamate (CIPC) to a potato storage facility. As noted in the Plant patent, CIPC is a solid at room temperature which is generally dissolved in polar solvents such as propylene glycol and, more recently, methanol. A typical weight of CIPC in solution is about 78% of the weight of the solution for commercial products using methanol as the solvent. A solution of CIPC was desired for forming aerosols of CIPC as well as for handling.

More recent patents relating to the application of CIPC to a storage facility are Sheldon and Morgan, respectively, U.S. Pat. Nos. 4,226,179 and 4,887,525. Sheldon involves a process for ultrasonically vaporizing a solution of CIPC, while the Morgan patent relates to an improved technique for moderating the air flow within a storage facility to get better distribution of CIPC aerosol produced from solvent-based system.

Sheldon refers to the possibility of applying non-solvent based CIPC. No example of such technique is given in Sheldon nor is there any suggestion as to how such a technique would be accomplished. Sheldon indicates that a solvent may be necessary in order to keep the chemical liquid in the spray nozzle. (Col. 4, lines 50 et seq.) The temperature range indicated by Sheldon for the CIPC is 70° F. to 250° F. (Col. 5, lines 1 through 13). The melting point of pure CIPC, however, is about 104° F. At Col. 9, lines 5 et seq., Sheldon indicates that the CIPC present should be at least 60% by weight and preferably 75% by weight of the chemical feed material with the remainder being solvent. Sheldon does not indicate that compressed air at about 70 psig. fed to the spray nozzle of his device be heated (Col. 10, lines 20 et seq.). The device of Sheldon utilizes a large quantity of air; 5000 cfm. is introduced into his misting device (Col. 10, lines 25 et seq.).

Sheldon notes that thermal fogging tends to produce large droplets of CIPC, cause degradation of the CIPC and warm the stored potatoes, which may promote bacteria growth.

The technique utilized in the Morgan patent involved thermal fogging prior to introduction of the fog of CIPC in the circulating air stream of a storage facility. Thermal foggers which have been commercially used are constructed similar to that illustrated in FIG. 1, wherein a propane flame burns within a hollow pipe (combustion chamber) which is enclosed by another generally cylindrical enclosure. It is into this outer enclosure that the solvent based CIPC is introduced. The solvent based CIPC is frequently introduced near the distal end of the combustion chamber with the solvent solution of CIPC being blended with the combustion gases emanating from the combustion chamber. This results in the solvent generally being evaporated and the CIPC being converted into a mixture of vapor (gas) and particles of CIPC, both liquid and solid particles.

The products of combustion exiting the combustion chamber are generally oxygen poor, so much of the methanol solvent is not burned. Thus, it evaporates and often decomposes to formaldehyde and formic acid, both of which are toxic. The products of combustion form a reducing atmosphere in a storage facility and further create an overpressure from the large volume of gases entering the facility. The reducing atmosphere causes the potatoes to be stressed, resulting in some of the starch being converted to sugars. Potatoes having a high sugar content yield french fries which are dark brown in color when cooked, especially at the tips of the french fries. This is generally undesirable and reduces the value of such stored potatoes. An over pressure results in much of the treatment chemical being vented from the storage facility.

As the Morgan patent noted, one of the problems had been that the CIPC tended to collect on the fans of the air circulation system of the storage facility as well as on the vent pipes and other portions of the facility. CIPC is not really effective for treating potatoes unless it is in contact with the potatoes, that is, deposited directly on the potatoes. The prior art thermal fogging system introduces into the potato storage facility all the products of combustion of the propane gas burner as well as evaporated methanol, or such other solvent, including decomposition products of methanol such as formaldehyde, formic acid and the like. Given that storage facilities are maintained at relatively low temperatures, in the neighborhood of about 40 to 50° F., these products, methanol, formic acid, formaldehyde, and the like, can liquify (condense) within the facility and can also be deposited on the potatoes. Since this can happen, it can also create a vapor pressure of these products within the storage facility long after a sprout inhibition treatment has occurred. Thus, a facility can be rendered unsafe for personnel to work in for quite some time. Although thermal fogging with thermal foggers of the type illustrated in FIG. 1 has been done for a long time, and storage sheds so treated have been relatively free of sprout growth, nevertheless the method is inefficient in its application of CIPC, i.e., CIPC decomposes to some extent, contaminates the storage facility with toxic, undesirable material, and is lost by venting.

Both Sheldon and Morgan involve methods and apparatus which introduce large volumes of gases, air or combustion products into a storage facility. This creates an overpressure within the facility and causes venting and loss of CIPC from the facility.

The technique of forming aerosols, i.e., a stable fog, of herbicides, pesticides, etc. has conventionally involved the use of solvents or carriers. In U.S. Pat. No. 2,460,792 of Pabst et al., the technique of adding a mixture of oils to obtain a stable aerosol is disclosed. A principal reason for the use of solvents with CIPC and similar sprout inhibitors apparently has been to accommodate the application of the sprout inhibitor as an aerosol and to facilitate handling of liquids by applicators.

While the Sheldon patent suggests the forming of a liquid particle "fog" by ultrasonic means, the technique has apparently not been practiced commercially and the patent is devoid of any instruction as how this is done from a non-solvent system. Current field techniques for commercial application of CIPC has been by fogging of a solvent solution of CIPC via a thermal fogger of the prior art type, frequently using moderated fan speed as taught by the Morgan patent.

SUMMARY OF THE INVENTION

The instant invention describes techniques, compositions and apparatus for the application of molten CIPC in the form of an aerosol to treat a vegetable storage facility. The molten CIPC is derived by melting substantially pure, solid CIPC. While CIPC has conventionally been provided as a solution of CIPC in a solvent such as a lower alcohol, e.g. methanol, or an oil such as peanut oil or the like, in order to form aerosols more readily, utilization of pure CIPC in molten form has advantages. This invention provides means and techniques for melting solid blocks of substantially pure CIPC at elevated temperatures, for example, temperatures greater than 150° F. and preferably greater than about 200° F. up to about 250° F. The molten CIPC is collected in a reservoir, which is maintained at a temperature of at least 105° F., which is the melting point of CIPC, and preferably at temperatures upwards of about 150° F. or more to maintain the molten CIPC in a highly flowable state.

Hot, liquid CIPC is collected in a sump to exit the CIPC reservoir and passed through a sieve or strainer where it is introduced into the intake of a pump, especially a peristaltic pump. The pump then conveys the molten CIPC through a heated, insulated conduit to an aerosol-forming device which converts the CIPC into an aerosol. The aerosol may be directed into the air circulation system of a storage facility or into a hot air stream which then enters the storage facility.

One type of device which may be utilized to convert the liquid, molten CIPC into an aerosol involves an appropriate nozzle which ejects a stream of molten CIPC which may be contacted externally of the nozzle with jets of hot, pressurized air. The air is generally at a pressure of above about 150 psig and a temperature above about 500° F. and at least a portion of it is ejected tangentially from the same nozzle. The compressed air is preferably above about 550° F. and is particularly effective at 600–650° F. and above. These pressures and temperatures are significantly higher than anything previously utilized or suggested, e.g., see Sheldon patent.

Another type of aerosol-forming device is one which combusts propane or butane or similar hydrocarbon gas whereby the molten CIPC is directed downstream of the burners such that the hot gases coming off the burner interact with the CIPC droplets to vaporize the CIPC and to form a stable aerosol. Unique results are achieved by the use of molten CIPC in such a system, as described hereinafter.

There are numerous advantages to utilizing solid CIPC as the starting material for treatment of potato storage sheds and the like. Solid CIPC is very safe to handle and may be readily made with a purity of greater than 98% chemically pure CIPC. Thus, there are few impurities or toxic materials which may be introduced into a potato storage facility from such solid CIPC. Also, solid CIPC is extremely safe to ship and to handle, in contrast to a solution of CIPC in an appropriate solvent, especially alcohol solvents. Solutions of CIPC are deemed hazardous materials for ICC purposes.

The use of solid CIPC as the starting material from which an aerosol is formed eliminates the introduction of alcohol, alcohol combustion products or alcohol decomposition products into a storage facility. These combustion or decomposition products may include formaldehyde, formic acid and other noxious chemicals. Solutions of CIPC and alcohol may contain from about 22% to about 50% by weight of alcohol. Various alcohols such as methanol, isopropanol and the like may be used. Thus, considerable noxious chemicals may be introduced into the storage facility from an alcohol-based CIPC solution regardless of the type of aerosol device used. Even evaporating alcohol from a CIPC solution and then pumping the molten residue may result in some alcohol retention such that upwards of perhaps 5% of the CIPC formed into an aerosol from such evaporation procedures may be alcohol or its decomposition or combustion products.

DESCRIPTION OF THE INVENTION

Figure 1:
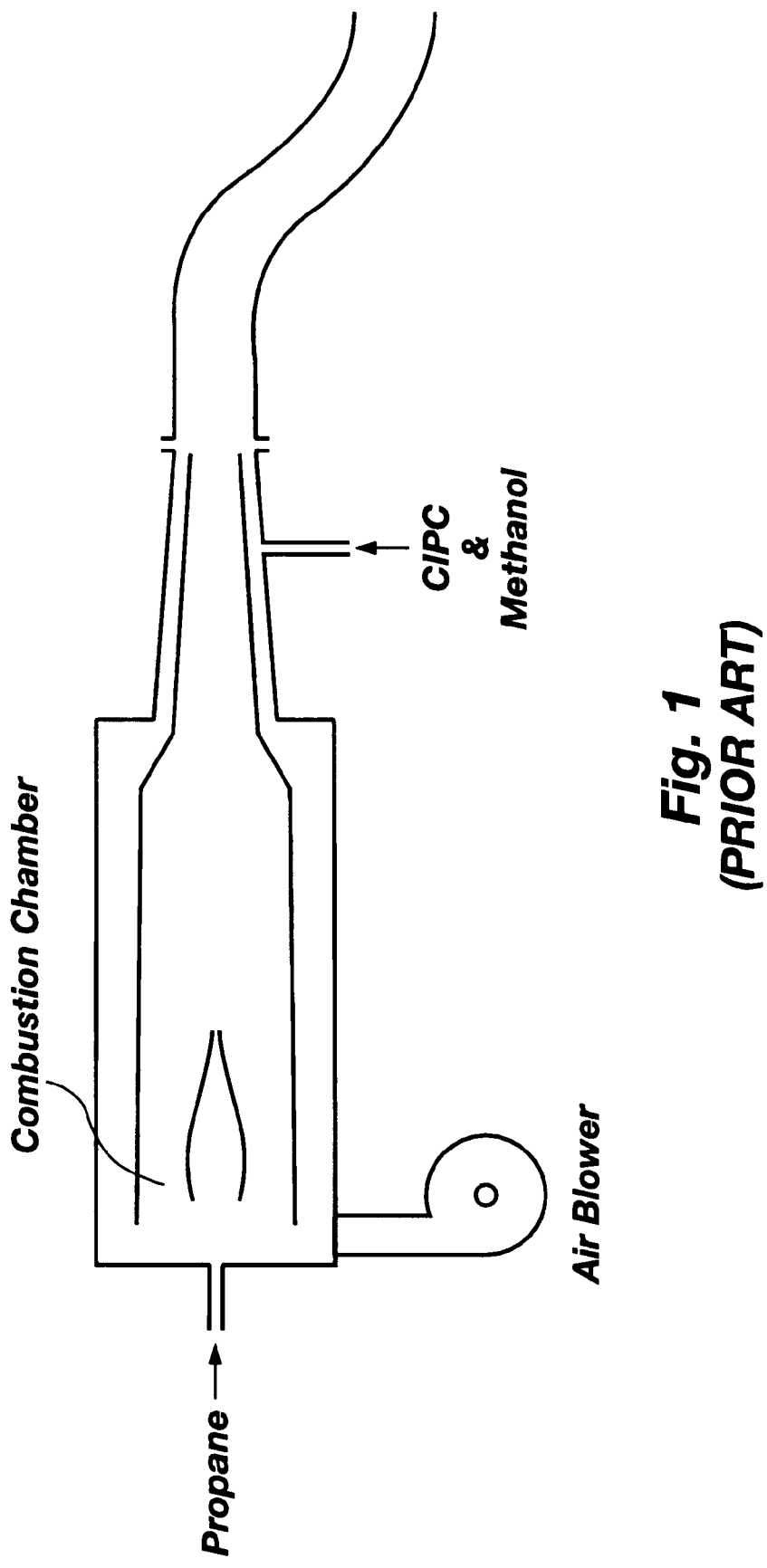
FIG. 1 is a schematic representation of a prior art, thermal fogging device for forming aerosols from CIPC solutions.

The instant invention involves the formation of an aerosol from molten, substantially pure CIPC derived by melting a solid mass of CIPC. The melting of the CIPC solid material, usually in the form of a block, although flakes or chips of CIPC may also be utilized, is accomplished by placing the block in a first hot zone which is at a sufficiently high temperature that rapid melting of the CIPC results. Solid chips or flakes of CIPC could be readily melted by exposing a porous basket to temperatures well above the melting point of CIPC. When molten CIPC is used to form an aerosol, the application rate of CIPC to a storage facility may be limited by the rate of melting of the CIPC block material. Thus, rapid melting permits rapid formation of aerosol and rapid treatment of a storage facility.

A second hot zone is preferably maintained which receives the molten CIPC which had melted in the first zone. The second hot zone may be maintained at a lower temperature, for example, about 150° F. compared to temperatures significantly in excess of 150° F., for example, about 200° F. in the first zone. The second zone is maintained at a temperature which provides the CIPC with substantial heat content as well as optimum fluidity. Heat content of the liquid CIPC is important to preclude freezing of the liquid at any point between the second hot zone and the aerosol-forming device.

The second hot zone is preferably located at a lower level in the same tank as the first hot zone so that molten CIPC drains by gravity directly from the first hot zone into the second. The CIPC from the second hot zone is pumped through an insulated and preferably heated line to an aerosol-forming device which forms an aerosol of the CIPC, which is then distributed through a storage facility via the normal air circulation system of the storage facility. The aerosol-forming device may be one of several types of devices as will be described more fully hereinafter.

CIPC is preferably provided in a solid form in a container such as a plastic bucket in which the top opening of the bucket has a greater diameter than the closed bottom of the bucket. The plastic bucket has a lid which makes good sealing contact with the rim of the top opening of the bucket. A block of CIPC may be placed in the first hot zone by removing the lid from the CIPC-containing bucket and turning the bucket upside down in the first hot zone. As the CIPC becomes warm and the air around the bucket warms the bucket, the bucket may be readily removed, allowing the block of CIPC to remain in the hot zone until it is totally melted.

The reservoir into which the CIPC melts has a volume which is greater, preferably, than a single block of CIPC. Thus, a second block of CIPC may be placed in the first hot zone and started to melt before all of the CIPC has been pumped from the second hot zone or reservoir.

Also, CIPC blocks may be provided as bricks in sealed plastic bags. The plastic bags are contained within a box which conforms to the shape of the brick. The box and bag may be used as a mold into which molten CIPC is poured. Alternatively, a mold may be used into which liquid (molten) CIPC may be poured. Such a mold may be lined with a plastic bag into which the CIPC is poured. Once the CIPC has cooled and solidified, the block of CIPC may be easily removed by removing the bag. The bag may then serve as part of the shipping container. The bag may be sealed and the enclosed block placed in an ordinary cardboard box having a shape and size similar to the block. In the event the solid CIPC encounters high temperatures, i.e., above the CIPC melting point during shipment, the CIPC remains within the plastic bag.

Further description of the invention may be facilitated by reference to the following drawings.

Figure 2:
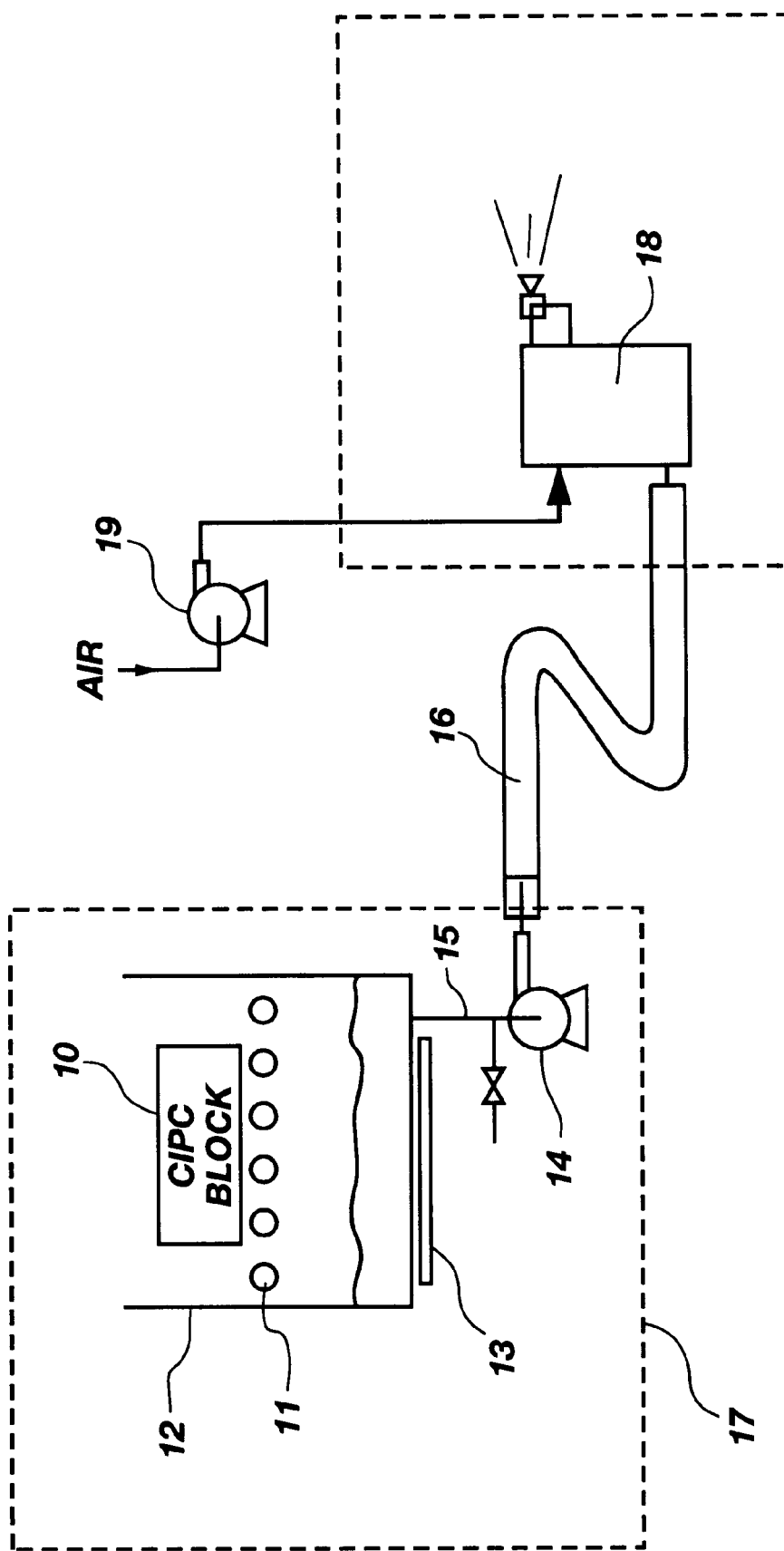
FIG. 2 is a schematic representation of a system for forming an aerosol from solid CIPC as the starting material.

FIG. 2 is a schematic illustration of a process and apparatus for practicing the instant invention. A block of CIPC 10 is shown resting on heating elements 11 in a tank 12. The tank preferably has a lid (not shown) to help maintain appropriate temperatures in the tank and to minimize the escape of the vapors of CIPC which may emanate during the melting of the CIPC. A plurality of heating elements 11 may be placed in the form of a grid or grill so that the block of CIPC may rest thereupon. Elements 11 are thermostatically controlled by a thermocouple and temperature controller so as to maintain the temperature of the heating elements generally between about 150–250° F. and preferably at about 200–220° F. CIPC melts at about 105° F. Maintaining a temperature approximately twice the melting temperature causes rapid melting of the CIPC even though the CIPC itself does not achieve a temperature much greater than 105° F. in the first hot zone.

The CIPC melts and drops into the bottom of tank 12, wherein the temperature is maintained at least 105° F. and preferably above 125° F. and generally at temperatures of about 150° F. or higher to maintain optimum fluidity and heat content for the CIPC. A heating element 13 may be secured to the bottom of the tank 12 with an appropriate thermocouple located in the tank or on the tank bottom adjacent the heating element and interacting with a temperature controller to maintain the temperature of the liquid CIPC at an appropriate level.

Molten CIPC in a highly flowable state is withdrawn from the tank 12 through a sump and a sieve (not shown in FIG. 1) into the intake of a pump 14. Preferably, a peristaltic pump is used for this purpose although other types of pumps may be used. The conduit 15 leading from the tank 12 to the pump 14 is of a plastic tubing, such as polyethylene, polypropylene, TYGON (vinyl tubing) or the like, having heat characteristics suitable for handling the temperatures involved with the molten CIPC. The pump discharge is conveyed through conduit 16, which is insulated and preferably electrically heated, to an aerosol-forming device. The pump 14 and tank 12 are preferably located in an insulated enclosure, as shown by dotted lines 17 in FIG. 2. The insulated enclosure has openings to make the top of the tank and the pump accessible. These openings are fitted with insulated doors. The heated tank maintains the interior of the insulated enclosure 17 at a sufficiently high temperature that the pump and lines within the enclosure, such as conduit 15, do not need to be insulated. The temperature of the space in the insulated enclosure 17 remains well above 105° F. because of the elevated temperature of the hot tank and the insulated enclosure.

A heat lamp is preferably included inside the enclosure to provide heat and light. It may be turned off if the temperature becomes too high. The lamp preferably is on any time a door to the enclosure is opened since cool air may enter the enclosure. Also, good visibility is desired if some component of the system inside the enclosure is being visually inspected. An interlock switch may be used for this purpose in connection with an enclosure door.

The molten CIPC passes through the insulated, heated conduit 16 where it is preferably maintained at a temperature of about 150° F. to enter an aerosol-forming device 18. The aerosol-forming unit 18 contains an electrically-heated heat exchanger which heats compressed air from compressor 19 to a temperature in excess of about 500° F. and preferably above 550° F. The compressor 19 compresses air to a pressure of at least about 150 psig and preferably at about 200 psig with a sufficient flow rate to form an aerosol with the CIPC through an appropriate spray nozzle. The spray nozzle is illustrated and described hereinafter.

The aerosol-forming device 18 illustrated in FIG. 2 is placed in a storage facility's air circulation system downstream of the air circulation fan. The air circulation fan speed is preferably moderated to cause an air stream flow which is about one-fifth to about one-tenth the normal velocity of air in the circulation system. The air flow in the storage facility's air circulation system is preferably generally laminar and not at a sufficient velocity to be in turbulent flow. As illustrated in FIG. 2, an aerosol of substantially pure CIPC is formed with air as the only added ingredient to cause an aerosol to occur. Thus, there are no contaminants of any type carried into the storage facility. It has been found that when a system of the type illustrated in FIG. 2 has been used to treat storage facilities, there is very little solid residue of material found on the floor of the fan house and the residue of CIPC on potatoes is excellent.

Treatment of potato storage facilities with sprout inhibitors such as CIPC usually occurs during cold weather.

Typically, potatoes are harvested in September and stored immediately. Within about three to four weeks after storage, usually in about mid to late October, the first treatment with a sprout inhibitor is conducted. The ambient outdoor temperatures during mid to late October in most potato-growing regions in the United States and of the world are generally below about 50° F. and are oftentimes much cooler than that. Typically, freezing temperatures are encountered during at least some of the treatment of a storage facility. Thus, the molten CIPC must be maintained at an elevated temperature, for example, above 125° F. and preferably near 150° F. during its transport from the melting tank to the aerosol-forming device. If the CIPC contacts any cold junctions, it will immediately freeze and plug up the system. Thus, it is important that the complete conduit between the CIPC pump and the aerosol-forming device be insulated and electrically heated. If two or more electrically-heated conduits must be joined, these junctions must be well insulated and preferably located inside insulated boxes or the like to avoid freezing of the CIPC. The CIPC melting portion of the system is located externally to a storage facility.

Figure 3:
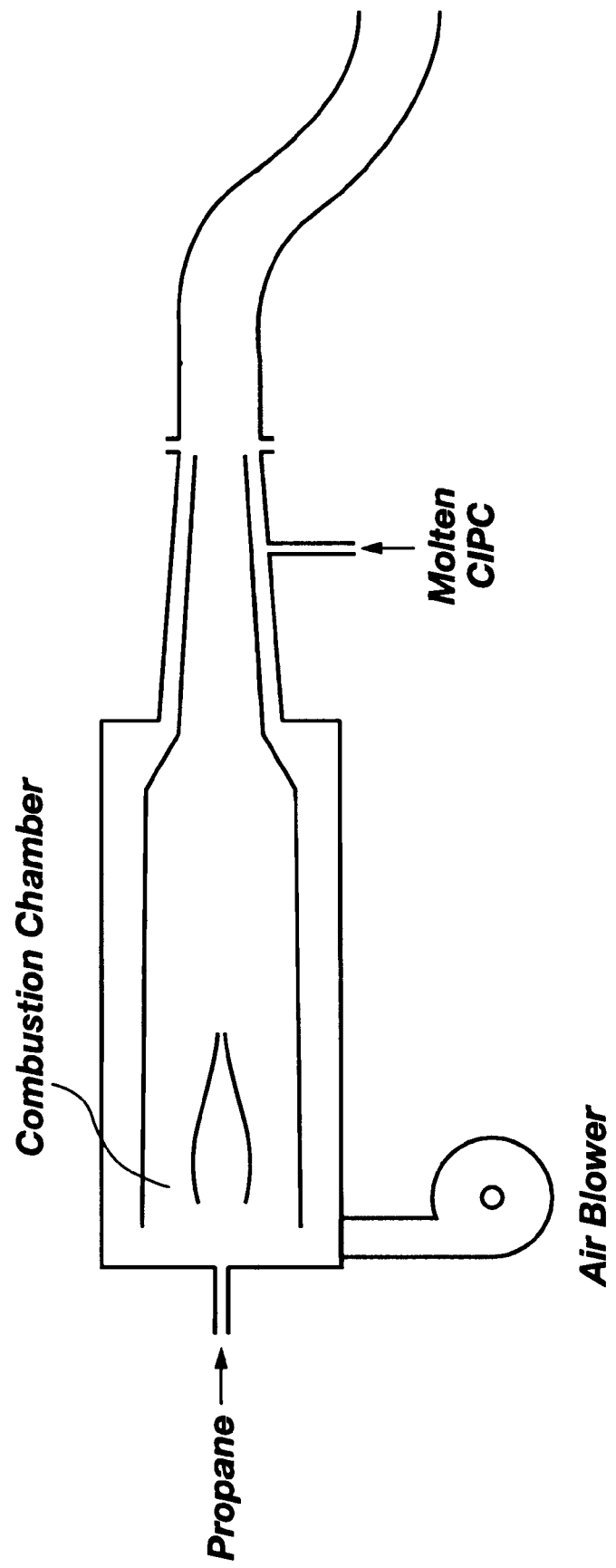
FIG. 3 is a schematic representation of a thermal fogging device for fogging molten CIPC.

As shown in FIG. 1, CIPC and alcohol had been conventionally fed into a combustion-type aerosol-forming apparatus thermal (fogger). In the unique process of the instant invention, molten CIPC is fed into such an apparatus. (See FIG. 3) Significant and unexpected advantages have accrued from this use of molten CIPC in a thermal fogger in comparison with aerosols formed by thermal fogging of methanol solutions of CIPC. The following advantages accrued from use of the molten CIPC with respect to a combustion-type fogging or aerosol-forming machine as illustrated in FIG. 3.

1. The combustion-type fogger could be run at a lower temperature than with a CIPC-solvent solution. Typically, combustion-type foggers are run at about 850–1000° F. in order to form an effective, stable spray of a methanol-based solution of CIPC, for example, one containing 22% methanol. In trials using molten CIPC, the combustion fogger operated very well at temperatures of about 750° F. and below. Fogging could be conducted at temperatures as low as 650° F. This is a significant advantage inasmuch as significantly less heat is put into the storage shed. It is desirable to keep stored potatoes at a temperature of about 42–45° F. to minimize sprouting. If extra heat is put in, this raises the temperature of the potatoes, which in a large mass takes days to return to a lower temperature. Thus, operation of a combustion fogger at temperatures as low as 650° F. reduces by 25% to 35% the heat energy typically put into a storage facility by thermal fogging of CIPC in solution.

2. Another advantage is that the system was more efficient. Typically, a combustion-type fogging device accepts about five gallons per hour of a 78% CIPC, 22% methanol solution. With molten CIPC as the feed material to the combustion fogger, flow rates of greater than six gallons per hour were easily achieved and rates of 7½ gallons per hour were achievable. This increases the output of the combustion-type fogger by at least about 20% to more than 35%.

3. No degradation products of alcohol were put into the storage shed; thus, the potatoes were not contaminated with any toxins. Also, since the combustion apparatus could be run at a lower temperature, less propane fuel was required, therefore, producing less $CO_2$ and CO. Also, because of the higher efficiency and higher flow rate of the CIPC, the fogger could be run for a shorter period of time, therefore, further putting less overall heat and less overall combustion products such as CO and $CO_2$ into the storage facility.

A system utilizing a conventional combustion or thermal fogging apparatus is illustrated in FIG. 3 wherein pure, liquid CIPC at a temperature preferably at about 150° F. or above is fed into the machine in a port normally used for feeding solvent-based CIPC. A stable fog of CIPC was formed at operating conditions of the fogger as low as 650° F. with flow rates as high as 7½ gallons per hour of pure, liquid CIPC. The CIPC may be at temperatures lower than 150° F. provided that a good throughput of flowable CIPC is maintained to the fogger. Generally, liquid CIPC at temperatures which approach the melting point, that is, temperatures approaching 105° F., is a more viscous material, which is more difficult to pump and may slow down the throughput.

There are advantages to each of the two systems described above. With the system of FIG. 2, only air and CIPC are directed into the storage facility. With the system of FIG. 3, existing combustion fogging devices can be utilized with pure, liquid CIPC and utilized more efficiently and less harmfully to the storage sheds than similar fogging units using solvent-based CIPC.

The system of FIG. 2 requires a good heat exchanger to heat the pressurized air, that is, air at a pressure of at least 150 psig, to temperatures of at least 550° F. and, preferably, at about 650° F. and above. The heat exchanger must withstand the high pressure of the air and, preferably, should be small enough that it may be placed in a small fogging unit which can be placed inside the fan house of a storage facility. Also, the fogging unit should be light enough that it can be carried readily by one or, at most, two people. The heat exchanger is preferably electrically powered so that only an electric power cable, the high pressure air hose and the insulated CIPC hose go into the storage facility. The air compressor and the melting apparatus for the system of FIG. 2 are located external to the storage facility. They may be located on a small trailer or in the bed of a pickup truck, for example.

Figure 4:
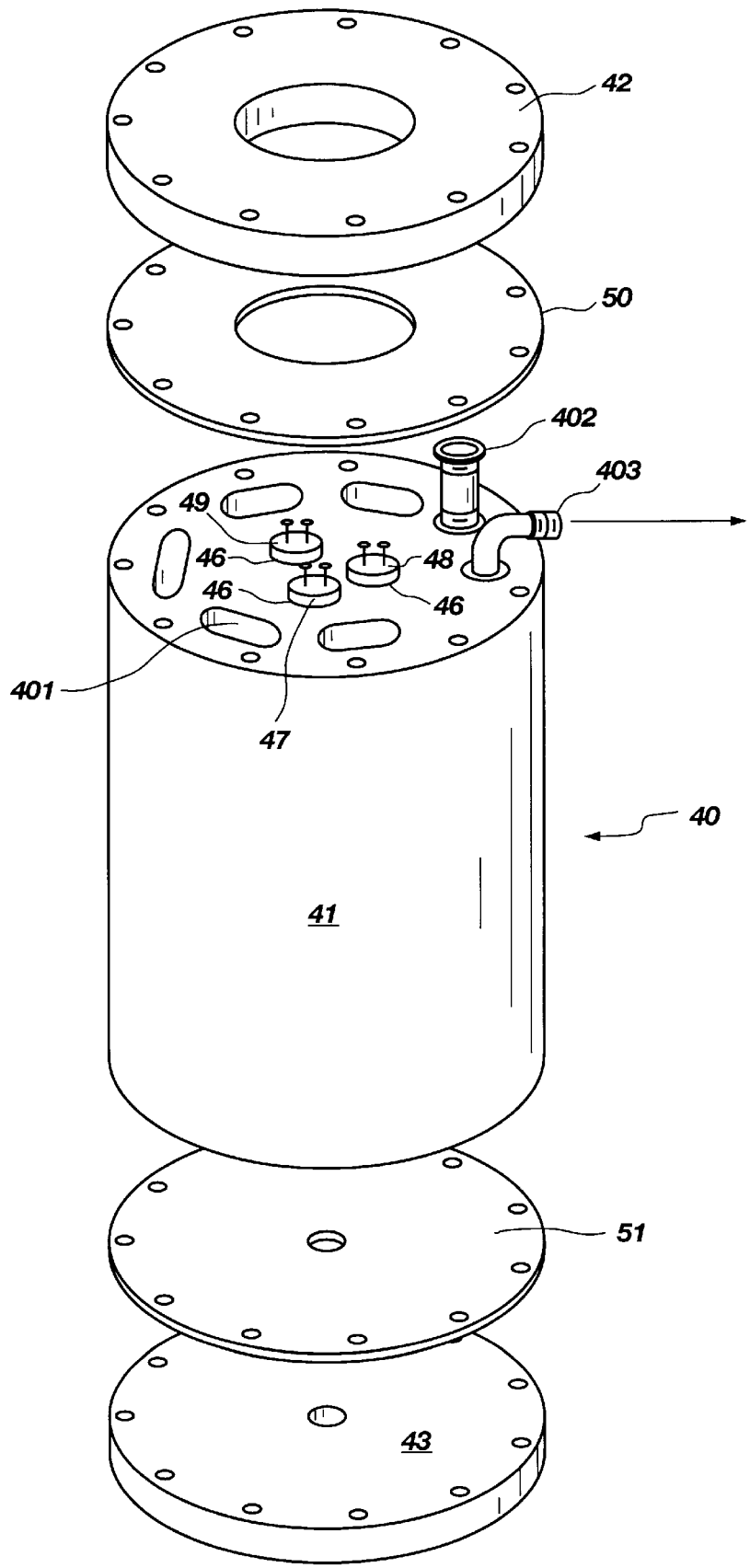
FIG. 4 is a perspective view of an electric-powered, compressed-air, heat, exchanger.
Figure 5:
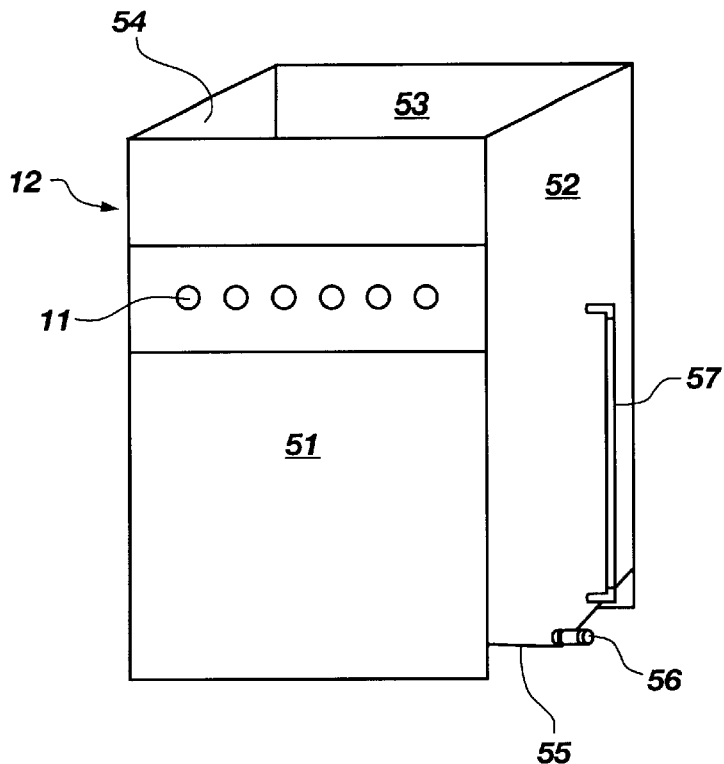
FIG. 5 is a perspective view of a melting tank for melting solid CIPC.
Figure 6:
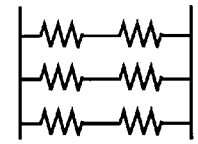
FIG. 6 is a circuit diagram of the heater elements.

A heat exchanger suitable for the purposes of this invention is illustrated in FIG. 4 wherein an aluminum, cylindrical body is used with multiple bores through the body to provide for multiple passageways for air. Flanges or heads are located at either end and gaskets are used to maintain a sealing condition so that the high pressure air is contained within the heat exchanger. The heat exchanger may be heated by bayonet heaters internally located or by pad-type heaters externally located or a combination of a pad-type external heaters and bayonet heaters may be used.

The cylindrical heat exchanger 40 is a high-pressure, high-temperature structure having a central body 41 with top head 42 and bottom head 43 bolted on each end. High-pressure, high-temperature gaskets 50 and 51 made of asbestos are used at each end of the central body. With precisely planed surfaces, gaskets may be eliminated. Also, the external seam may be welded.

The central body and head are preferably made of heavy-duty aluminum although other light-weight, strong metals such as titanium, magnesium alloys, and the like may be used. Metals particularly useful are those which may be readily cast and machined and which have good strength and heat conductivity. Generally, air pressures in the range of 150 to 200 psig. are sufficient to cause an effective, stable aerosol to be formed by the use of nozzles such as that illustrated in FIGS. 8 and 9. The heat exchanger 40 must be susceptible to withstanding temperatures of up to about 800° F. An exit air temperature of at least about 550° F. is desired while exit air temperatures of about 600° F. to 650° F. are especially desirable.

The central body 41 has a multitude of central bores 44, 45 and 46 which accommodate bayonet heaters 47, 48 and 49, each having a power rating of about 1000 to about 2000 watts at 220 volts. The temperature of the exit air is sensed by a thermocouple which interacts with a controller which controls power to the bayonet heaters. The mass of the heat exchanger serves as a heat sink. The surface temperature of the heat exchanger may also be sensed by a thermocouple which via a controller may prevent the heaters from overheating. While the bayonet heaters are designed to withstand surface temperatures of up to about 1000° F. or higher, the surface temperature is typically controlled at about the block temperature, which is about 650° to 700° F.

The bayonet heaters are selected to have a power rating (BTU's/hr or watts) approximately twice that typically required to heat a flow rate of 10 to about 25 and typically 10 to 15 cfm of high pressure air to temperatures as high as about 700° F. If a single bayonet heater fails, sufficient heating capability remains to permit continued use of the system. As stated elsewhere herein, once treatment of a storage facility is started, it is very desirable to be able to finish the treatment uninterrupted. The setup, dismantling and cleanup of the system of FIG. 2, or that of FIG. 3, is time consuming. Thus, it is very desirable not to have to shutdown and restart the system.

Generally, at least six air passages (bores) are present in the central body of the heat exchanger although ten, twelve or more air passages may be used. The bore diameter for each passageway is about ⅝ to about ¾ inches. It is desirable to maintain a high velocity of gas flow in the passageways to enhance heat transfer. Also, because of the high pressures involved, small diameter passageways are generally preferred. The passageways are generally located peripherally around, i.e. outboard, of the heating elements.

The individual passageways (bores) in the central body are connected, in pairs by grooves or channels 401 which connect all the passageways to permit a continuous flow of air from the inlet fitting 402 to the outlet fitting 403. The ends of the central body and the faces of each head 42 and 43 are machined so that an air-tight seal is effectuated with gaskets interposed between the body ends and head faces. Turbulators may be used in the passageway to increase turbulence to increase heat transfer.

The heads 42 and 43 are bolted to the central body. Insulation is generally wrapped or placed around the exterior of the heat exchanger to conserve energy and to maintain steady, elevated temperatures for the high-pressure air departing the heat exchanger.

The insulated CIPC fluid conduit may be led into an insulated housing which encloses the heat exchanger. The insulated CIPC fluid lines may be run in the heat exchanger enclosure without risk of the CIPC temperature dropping below about 150° F.

Generally, it is desired that hot, compressed air be fed to the aerosol-forming nozzle before CIPC is pumped to the nozzle. The hot air warms the nozzle and ensures that liquid CIPC in the nozzle does not freeze. The aerosol-forming nozzle is preferably located closely adjacent the heat exchanger housing so that any uninsulated conduit carrying CIPC to the nozzle is very short. Because of the elevated temperatures inside the heat exchanger housing, CIPC in the liquid conduit line exiting the housing may be at a temperature well in excess of 150° F. Preferably, the CIPC conduit line connected to the nozzle is metal so that heat from the hot nozzle is conducted along the CIPC line toward the heat exchanger enclosure to further minimize the possibility that CIPC will freeze in the exposed line.

An especially useful melting apparatus is illustrated in FIG. 5. The apparatus includes a tank 12 which is substantially square in cross-section and constructed from four steel panels 51, 52, 53 and 54 which form the tank sidewalls. The bottom 55 of the tank is V-shaped with the trough of the "V" sloping towards the discharge outlet 56. A transparent, tubular sight glass 57 is attached to the tank with its lower end near the bottom of the tank so that the level of liquid CIPC in the tank can be seen.

Six bayonet heating rods 11 pass horizontally through opposed tank sidewalls about ⅔ of the height of the vertical sidewalls from their lower edge. The heating rods are thermostatically controlled to maintain a temperature of 220° F. at their surface, which is sufficient to melt a 25 lb. block of CIPC in about 15–25 min. A total of about six to seven thousand watts is generally sufficient for such a purpose. The wattage is such that the power is cycled frequently by the thermostatic control to control the rod temperature at a desired level. Heaters with less wattage could be used, however, the heaters would remain on for longer periods of time and the preciseness of temperature control may be diminished and a longer initial heat-up time would be required. The heater system is first heated to the desired temperature and air is introduced which reduces the heater temperature. The higher wattage heaters permit rapid recovery of the desired temperature.

Typically the heating rods (elements) are wired with three pairs of heating rods wired in parallel. Two rods are wired in series with one another to form each pair of rods. A simplified wiring diagram is illustrated in FIG. 6. In FIG. 6, each heating rod is illustrated as a resistor. Typically, 220 volt power is utilized. Excess heating capacity is desirable to achieve rapid melting. Also, once CIPC treatment of a storage facility has begun, it is very desirable to complete the treatment without having to shut down. Thus, excess heating capacity is desired in the event a heating rod burns out.

The rods are generally evenly spaced from one another to form a grill which supports a large block, e.g. a 25 lb. truncated cone, of CIPC. Anywhere from four to eight rods may be utilized. The grill preferably supplies a support area of at least about 12×12 inches. The cross-sectional area of the tank is preferably at least about 14×14 inches. The heating rods are supported on both ends by opposed sidewalls of the tank.

An overhead space at least about ten inches high exists above the grill support. Below the grill is a cavity at least about 12 inches deep. This cavity provides a reservoir for molten CIPC. It is preferably maintained at a temperature of at least about 150° F. by pad-type electric heaters 13 (See FIG. 1) thermostatically controlled. The pad heaters are secured against the exterior of the sloped panels of the tank bottom. The melt time and the capacity of the molten CIPC reservoir must be sufficient to meet the CIPC flow rate requirements.

The discharge outlet 56 is located at the lowest point in the tank. A sieve or screen (not shown) is located over the discharge opening to prevent solid chunks of CIPC from getting into the lines. Molten CIPC which drops through the heating rod grill often does so in the form of soft solid chunks, which transform to fully liquid material in the heated reservoir. The flexible tubing leading from the melting tank to the pump and from the pump discharge generally have a small interior diameter e.g., from about ¼" to ⅜" although larger lines could be used. Thus, these lines could easily be plugged by solid material. A sieve or screen placed in the line to the pump having openings of about 1/8" or less is sufficient to prevent solid material from being discharged from the tank.

The chunks of CIPC are heavier than the molten CIPC and tend to rest on the bottom of the tank where the pad heaters are effective to melt the chunks.

The tank discharge tube connects the discharge opening to the molten CIPC pump. Preferably the pump is a peristaltic pump which acts on flexible tubing to force molten CIPC through the tubing.

Figure 7:
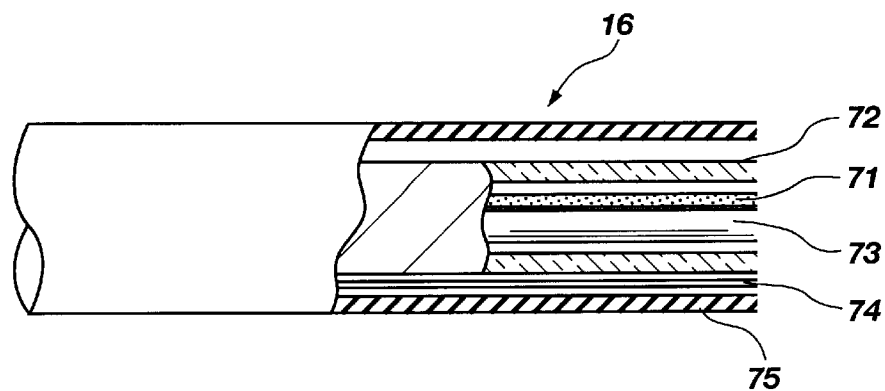
FIG. 7 is a cross-sectional view of a heater, insulated conduit for conveying molten CIPC.

In FIG. 7, a heated, insulated tube assembly 16 is illustrated. Flexible plastic tubing 73 is at the core of the assembly. A heat tape 71 is strung longitudinally along the plastic tubing 73. Fiberglass insulation 72 having a thickness of about 1/4" is wrapped around the tubing and heat tape. The insulation is then wrapped with a thin, plastic film strip 74 before this sub-assembly is pulled into a flexible, rubber hose 75 having a large interior diameter, e.g. an I.D. of about 3/4".

The insulated, heated conduit through which molten CIPC is conveyed to an aerosol device. Heat tape 71 and flexible insulation 72 encompasses the flexible tubing 73, which has a diameter of about 1/4" to 3/8". If an especially long run of heated conduit 16 is required to convey molten CIPC to an aerosol device, insulated and heated junctions may be required since heat tape is usually available only to certain maximum lengths, e.g., up to about 30 feet. An additional heat tape may be required which can be connected in series with the first heat tape. Thus, the insulated, heated conduit is sized in length to match that of commercially available heat tape. Each length of such conduit is equipped with connector fittings on each end.

A first heated, insulated conduit is connected to the pump discharge tubing inside the melt tank insulated housing so that the connection remains well above 105° F. An additional length of heated, insulated conduit may be connected to the first conduit by making such connection in an insulated environment, e.g., in an insulated box or with insulation wrapped around the connection. Having the connection in an insulated box allows the connection to be readily checked visually to be certain no leakage is occurring. Also, an insulated box permits easy manual joining of the connectors of the respective conduits.

Figure 8:
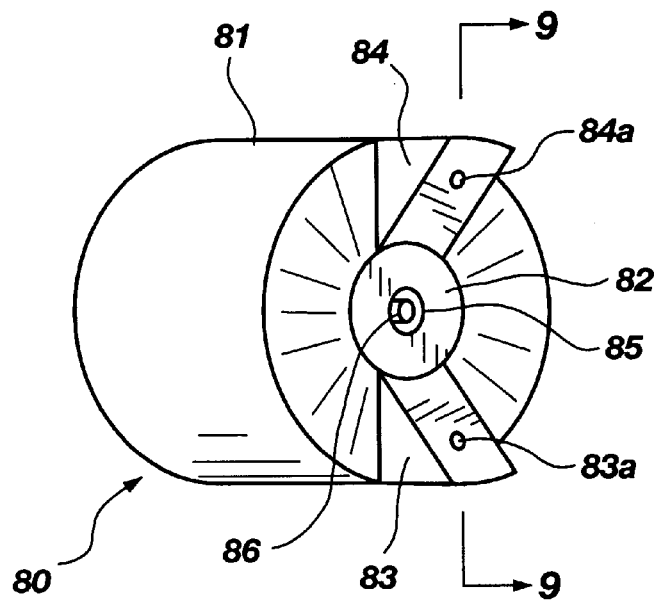
FIG. 8 is a perspective of a spray nozzle for forming an aerosol of molten CIPC.
Figure 9:
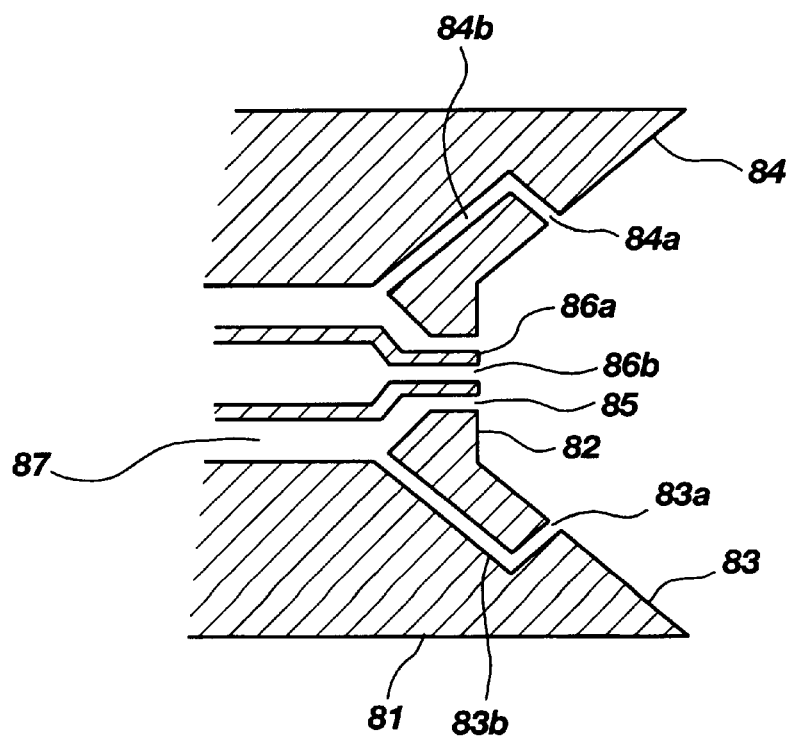
FIG. 9 is a cross-sectional view along section lines 9—9 of the nozzle of FIG. 8.

A particularly useful nozzle for effecting an aerosol of molten CIPC and hot, high pressure air is illustrated in FIGS. 8 and 9. The nozzle 80 is structured so that the molten CIPC and air mix externally to the nozzle. The nozzle cap 81 has a pair of wings 83 and 84, which extend laterally and forward from the nozzle face 82. The nozzle face has a central bore 85 in which an ejector 86 is located. The bore I.D. is larger in diameter than the injector O.D. The ejector is hollow and its tip 86a has an opening 86b through which liquid CIPC is ejected. The ejector opening 86b is substantially flush with the face 82 of the nozzle. Nozzle bore 85 opens as an aperture in the nozzle face concentrically about the ejector tip 86a. Hot, high pressure air flows through the bore, warming the CIPC ejector and discharges around the CIPC stream flowing from the ejector. This air-CIPC stream is contacted externally from the face of the nozzle by a pair of hot, high pressure gas streams propelled at acute angles to the CIPC stream from ports 83a and 84a located in the nozzle wings 83 and 84. The air passage ways 83b and 84b leading to ports 83a and 84a interconnect with the main air-carrying bore 87.

The compressed, hot air is funneled through nozzle bore 87, through passageways 83b and 84b to be ejected through ports 83a and 84a to impact the CIPC ejected through ejector opening 86b at a region external to the nozzle face 82. The angle of ejection of air from ports 83a and 84a is about 45 degrees to the ejected CIPC stream. A portion of the air in base 87 passes annularly about eject tip 86a to help propel CIPC away from the nozzle face. The parallel air flow and the two tangential impacting air streams rapidly converts the liquid CIPC to a stable aerosol.

What is claimed is:

1. A method for treating a potato storage shed with an aerosol of CIPC sprout inhibitor comprising:

a) melting a solid CIPC sprout inhibitor at a temperature greater than about 105° F. in a heated zone to form molten CIPC sprout inhibitor;

b) collecting said molten CIPC sprout inhibitor in a reservoir;

c) maintaining the temperature of the molten CIPC sprout inhibitor in said reservoir at a temperature above about 105° F.;

d) conveying said molten CIPC sprout inhibitor from said reservoir through a heated conduit to maintain the temperature of said molten CIPC sprout inhibitor at a temperature greater than 105° F. to an aerosol-generating device, wherein said heated zone and said reservoir are located within an insulated enclosure and wherein said aerosol-generating device is located outside of said insulated enclosure;

e) forming an aerosol consisting essentially of said molten CIPC sprout inhibitor in said aerosol-generating device; and f) directing said aerosol of CIPC sprout inhibitor into a potato storage shed.

2. The method of claim 1 wherein said solid CIPC contains at least 98% chemically pure CIPC.

3. The method of claim 1 wherein said solid CIPC is a block of CIPC having a mass of about ten pounds.

4. The method of claim 1 wherein said heated zone is maintained at a temperature above about 125° F.

5. The method of claim 1 wherein said heated zone is maintained at a temperature above about 150° F.

6. The method of claim 1 wherein said heated zone is maintained at a temperature above about 200° F.

7. The method of claim 1 wherein the temperature of said molten CIPC sprout inhibitor in said reservoir is maintained at a temperature above about 125° F.

8. The method of claim 1 wherein the temperature of said molten CIPC sprout inhibitor in said reservoir is maintained at a temperature above about 150° F.

9. The method of claim 1 wherein the molten CIPC sprout inhibitor in said heated conduit is maintained at a temperature above about 125° F.

10. The method of claim 1 wherein said aerosol-generating device is a combustion fogger aerosol-generating device.

11. A method for spraying an aerosol of molten CIPC sprout inhibitor comprising:

a) melting solid CIPC at a temperature of at least about 110° F. to form liquid CIPC sprout inhibitor;

b) transporting said liquid CIPC sprout inhibitor through heated tubing at a positive pressure and a temperature of at least about 110° F. to a spray nozzle;

c) injecting air at a temperature of at least about 550° F. and a pressure of at least about 150 psig into said nozzle; and d) directing said molten CIPC sprout inhibitor through a central exit opening in said nozzle and circumferentially exiting said air from said nozzle around said ejected CIPC and directing at least a pair of compressed gas streams tangentially to contact said central air-CIPC sprout inhibitor stream externally to said nozzle to form an aerosol containing said CIPC sprout inhibitor.

12. The method of claim 11 wherein the compressed air flow rate to said nozzle is adjusted to the molten CIPC flow rate to obtain an aerosol.

* * * * *